United States Patent [19]

Abrams et al.

[11] Patent Number: 5,769,778

[45] Date of Patent: Jun. 23, 1998

[54] MEDICAL MAGNETIC NON-CONVULSIVE STIMULATION THERAPY

[75] Inventors: Richard S. Abrams, Chicago, Ill.; Conrad M. Swartz, Johnson City, Tenn.

[73] Assignee: Somatics, Inc., Lake Bluff, Ill.

[21] Appl. No.: 888,494

[22] Filed: Jul. 7, 1997

Related U.S. Application Data

[63] Continuation-in-part of Ser. No. 231,307, Apr. 22, 1994, and Ser. No. 784,127, Jan. 15, 1997.

[51] Int. Cl.[6] .................................................. A61N 1/00
[52] U.S. Cl. .............................................. 600/14; 128/897
[58] Field of Search .................. 600/9–15; 128/897–98; 607/45

[56] References Cited

PUBLICATIONS

Mansfield et al, "NMR Imaging in Biomedicine", Apr. 13, 1982, pp. 297–332.

*Primary Examiner*—John P. Lacyk
*Attorney, Agent, or Firm*—Eliot S. Gerber

[57] ABSTRACT

A medical device includes a magnetic stimulator having a magnetic induction coil which is placed next to the scalp of a patient. A pulse train of high energy electrical waves is flowed through the induction coil to produce a sufficiently strong magnetic field to generate currents in the patient's brain for the therapy of psychiatric illnesses. These currents induced in the brain are below the minimum needed to induce a convulsive brain seizure. The device includes an ECG (electrocardiograph) to monitor the electrical activity of the patient's heart and an EEG (electroencephalograph) to monitor the patient's electrical brain waves.

14 Claims, 3 Drawing Sheets

MEDICAL MAGNETIC NON-CONVULSIVE STIMULATION THERAPY

RELATED APPLICATION

This is a continuation-in-part application partly based on application Ser. Nos. 08/231,307, filed Apr. 22, 1994, and 08/784,127, filed Jan. 15, 1997.

FIELD OF THE INVENTION

The present invention relates to medical methods and more particularly to a method of generating electrical currents inside the brain of a human patient without inducing brain seizures in order to treat certain psychiatric disorders, especially psychotic depression.

DESCRIPTION OF THE RELAYED ART

The related art discloses various methods used in the past for inducing brain seizures in patients for the treatment of certain neurologic and psychiatric disorders ("neuropsychiatric disorders"), particularly certain types of psychotic depression. For example, brain seizures may be induced in human patients by the injection of chemical convulsant agents (pentylenetetiazol), the inhalation of gaseous convulsant agents (e.g. flurothyl, Regan U.S. Pat. No. 3,976,788), or by the application of electric currents to the scalp in a procedure termed electroconvulsive therapy (ECT), sometimes referred to as "shock therapy". Only ECT is still used to induce therapeutic brain seizures.

In addition, various pharmacological agents (drugs) such as imipramine, lithium, perphenazine, etc. have often been used to treat psychotic depression. However, sometimes such pharmacological agents have adverse side effects, deadly overdose risks, or are not reliably effective.

In a present method of ECT, a pulsed or varying current of controlled amperage or controlled voltage is applied through electrodes to the patient's head for a period of 1–10 seconds. There are several hazards and risks with ECT, however; these include:

1) The electrical resistance of the skull to the passage of current greatly attenuates the amount of current that actually reaches the brain. The rest of the current is shunted through the skin and scalp. Increasing the amount of current applied to the head, to reach the minimum required to induce seizures, may result in burns to the scalp and skin from the shunted current.
2) Because the direct passage of electric current through the relatively high-impedance skin during ECT can cause skin burns, the doctor must reduce the impedance of the electrode-to-skin interface by first cleansing the skin, then wiping the skin dry, and applying conductive gel over the metal electrode surfaces and their application sites on the skin. Special effort is then required of the doctor to ensure that the metal disc electrodes are applied firmly to the skin, either by holding them in place with a rubber headstrap, or holding them with manually-applied non-conductive electrode handles. Alternatively, self-adherent, solid-gel disposable stimulus electrodes can be used, after first cleansing the skin and then wiping the skin dry. Metal disc electrodes, rubber headstraps, nonconductive electrode handles, and disposable self-adherent stimulus electrodes are all costly to purchase and time-consuming to maintain and use.
3) The attenuated current that finally penetrates the skull is often capable only of stimulating seizures over the surface (cortex) of the brain. These seizures must then spread by secondary means to the deeper brain structures where the therapeutic effects of a seizure are believed to occur. Often these secondary means of spreading are insufficient to induce therapeutic remission of the disorder.
4) It has been reported that memory loss may accompany the passage of current through the temporal lobes of the brain as part of the procedures of ECT.
5) Leakage currents from defective equipment may reach the patient through the electrodes. Such leakage currents are dangerous to patients with cardiac arrhythmias or pacemakers. This requires that the ECT equipment undergo regular, and expensive, inspections and calibration checks.
6) The negative feelings, stigma, and fear held by much of the public to the phrase "hock therapy" causes many patients to refuse the treatment although it would be beneficial to them.
7) All convulsive therapies, including ECT, induce generalized brain seizures that stimulate superficial and deep subcortical brain structures indiscriminately. In some neuropsychiatric disorders for which ECT is used, however, it appears that only the deep brain structures (e.g. the diencephalon) that function abnormally and therefore require stimulation. Unnecessary stimulation of brain structures accordingly increases only the possibility of undesired effects (see next paragraph).
8) Generalized seizures have hemodynamic consequences (hypertension, tachycardia, increased intracranial pressure) that can present undesired and sometimes unacceptable risks to patients with pre-existing cerebral, cardiovascular, or cerebrovascular conditions (e.g. myocardial infarction, hypertension, stroke, brain tumor). These result from the spread of seizure activity into brain areas that control cardiovascular excitation, such as the medulla. Patients with brain lesions, as from cerebrovascular disease, can suffer substantial confusion and memory loss from the spread of seizure activity into brain regions that contain those lesions.

NCEST (nonconvulsive electrical stimulation therapy) applies a pulsed current of constant low amperage or voltage. This stimulates surface and deep brain structure, but does not induce brain seizures because of the low energy used. When used at particularly low current it may act by direct stimulation of tissues only outside the central nervous system (CNS) and only indirect stimulation of the CNS. However, NCEST suffers from many of the drawbacks that appear in ECT, and, in addition:

1) The low energy current often fails to penetrate the bony skull in sufficient dosage to stimulate the deep subcortical brain structures that are believed to require the most stimulation. Any increase in the amount of current used increases the risk of the undesirable side-effects of generalized brain seizures that occur in ECT.
2) The electric currents used in NCEST (and also in ECT) tend to diffuse through the brain as in a volume conductor.

This means the current is dispersed fairly evenly throughout the brain and cannot be focused, or concentrated, in a specific deep brain region, such as the diencephalon, to cause a therapeutic stimulation in just that region.

3) Even the low energy currents used in NCEST may cause painful sensations in the skin and scalp that require the use of general anesthesia. The use of general anesthesia has been reported to cause mortality rates of approximately 0.001% consequent to gastric paresis with vomiting and aspiration pneumonitis, hypotensive cardiovascular collapse, or cardiac ischemia or cerebral anoxia from laryngospasm.

In U.S. Pat. No. 5,066,272 to Eaton et al, incorporated by reference, a magnetic nerve stimulator produces rapid chain high amplitude voltage discharges to a coil placed near a patient's scalp to generate a magnetic field. The patent asserts that the brain's high-level cognitive functions are disrupted for diagnostic purposes, i.e., to map functional areas of the brain.

In U.S. Pat. No. 4,940,453 to Cadwell, incorporated by reference, a coil placed on a patient's head is electrically pulsed to produce magnetic stimulation. The magnetic stimulation generates an evoked potential. The evoked potentials are detected by electrodes connected to the arm and hand. The device is intended as a substitute for an electrical stimulator.

In U.S. Pat. No. 5,092,835 to Schurig et al a subject wears a hat having permanent magnets. The subject watches a monitor which provides audio and visual stimulation and holds electrodes in his hands to provide electrical pulses. The asserted purpose is to stimulate and repair nerve cells.

BRIEF SUMMARY OF THE INVENTION

The present invention comprises a method for stimulating surface, intermediate, or deep brain structures by the application of pulsed magnetic fields near the outside surface of the patient's head, e.g., transcranial magnetic stimulation therapy for the relief of psychiatric disorders, especially depression. There is no attempt to treat or diagnose neurologic disorders. The generated magnetic fields induce corresponding electrical fields in surface and deep brain structures, thereby depolarizing nerve cells and raising their level of excitation closer to the point of neuronal discharge. In nonconvulsive magnetic stimulation (NCMS), the intended therapeutic agent is low-energy excitation of one or more brain structures without the induction of a generalized brain seizure. This might be given under circumstances of pretreatment of the patient with one or more anticonvulsant pharmaceutical agents to inhibit the development or spread of partial or generalized seizure activity.

The nonconvulsive TMS device has electrodes which are connected to the chest of the patient to detect the patient's heart beat. They are preferably conventional ECG (electrocardiogram) electrodes. The device also has EEG (electroencephalograph) electrodes which are connected to the scalp of the subject. The device consequently is a combination of (i) a magnetic stimulator, (ii) an ECG monitor, and (iii) an EEG monitor. The ECG and EEG preferably include analog-to-digital converters, a CPU (Central Processing Unit) and a software program which detects the onset of a convulsion or calculates the risk of development of a convulsion and which automatically halts the magnetic stimulation before the convulsion occurs.

One important reason for incorporating an EEG monitor in a nonconvulsive TMS device is to be able to monitor the progress of an inadvertently-generated focal or generalized seizure in the occasional patient who is so predisposed. To date, there are five published instances, of which we are aware, regarding unanticipated seizures occurring in patients receiving nonconvulsive TMS for neurological evaluation. It is logical that there have been additional instances of focal seizures which were not detected because no EEG monitor was used. It is expected that the risk of seizure may be even greater with the prolonged stimulation required for treatment of psychiatric disturbances. In addition to causing fractures, dislocations, cardiac arrhythmias, cerebral anoxia, cardiac ischemia, and mental confusion, an unprotected grand mal seizure might progress to status epilepticus, with potentially severe—even permanent—sequelae. Termination of such a seizure requires administration of intravenous anticonvulsant agents under EEG control.

An ECG monitor is also important because nonconvulsive brain stimulation has been associated, in the ECT literature, with cardiac slowing (bradycardia), and even cardiac standstill (arrest). This occurs because nonconvulsive electrical stimulation can have a direct inhibiting effect on the heart via the vagus nerve. In addition, the ECT demonstrates evidence of seizure activity affecting the medulla, by tachycardia through right medullary stimulation or bradycardia through let medulla stimulation. Accordingly, heart rate disturbances seen on the ECG monitor can indicate seizure activity.

The EEG monitor is sensitive to electromagnetic interference (noise) as it detects brain waves at the microvolt level. The pulsed magnetic coil, potentially, is a source of such noise. There are a number of possible solutions of this problem. First, the EEG monitor is equipped with a notch filter which filters out wave forms at the frequency of the magnetic pulses. The notch filter preferably is automatically changed, under CPU control, if the pulse rate is changed. For example, if the pulse rate is in the frequency 25–50 Hz the notch filter would cancel all waveforms above 20 Hz. Secondly, the pulse frequency may be raised to above 50 Hz and a notch filter used to eliminate waveforms above 50 Hz. Thirdly, the pulse train to the magnetic coil may be halted and the EEG monitor activated only during pauses in the pulse train. For example, a pulse train of 5 seconds, a pulse of 1 second for the EEG detection, and another pulse train of 5 seconds, pause of 1 second and a third pulse train of 5 seconds.

In the method of the present invention a storage capacitor is discharged into a stimulating coil by means of one or more solid-state switches. The coil is positioned next to the head of the patient. The current in the coil generates a magnetic field pulse that induces a secondary current in the brain tissue. This secondary current may be focused on a specific region in the brain by selectively manipulating the position of the coil three dimensionally around the patient's head.

The voltage waveshape of the secondary current induced in the brain tissue is proportional to the rate of change of the magnetic field pulse. The delivered pulse, in NCMST, for example, may be a biphasic sine or cosine pulse with a duration of preferably 100 to 300 microseconds (usec). The pulse repetition rate is preferably 3 to 90 Hz and most preferably about 5 to 20 Hz. The pulse train is preferably applied for about 0.1 to 60 seconds, most preferably for about 10–20 seconds. The primary coil current is in the preferred range of 2000–5000A and the power is in the preferred range of 500–1500 watts. The magnetic flux density of the primary coil is preferably in the range of 1 to 5 Tesla, and most preferably about 2 Tesla.

The most preferred stimulus for nonconvulsive magnetic stimulation therapy (NCMT) is a 10 to 20 second biphasic pulse train at a frequency of about 3 to 20 Hz (pulsewidth in the range of about 50–300 microseconds). The several advantages of the method of the present invention are as follows:

1. Because the present method does not apply electric currents to the skin, NCMST does not expose the subject to the risk of skin burns.
2. Because the magnetic fields require no direct contact with the skin, time-consuming skin preparation is unnecessary and no costly stimulus electrodes or accessories are required.
3. Because the bony skull does not significantly impede the transmission of magnetic fields, there is no attenuation of the therapeutic stimulus before it reaches the deep brain structures: the intended strength electrical field current is directly induced in the brain region specified with NCMST.

4. Because magnetic fields can be oriented in three dimensions, to induce focused electrical field currents in deep brain structures, there is no necessity for the spread, and consequent attenuation, of brain tissue excitation from superficial to deep structures during the application of such magnetic fields.

Similarly, in patients with brain lesions, as from cerebrovascular disease, the brain stimulation can be focused in the selected areas, and unnecessary stimulation of brain regions near the lesions can be avoided, thereby decreasing risks of confusion and memory loss.

5. Because the invented method does not pass external electric currents through the temporal lobes, its use would not cause the same deleterious memory effects that have been reported in some cases from ECT.
6. Because the present method does not apply electric currents to the skin, the patient receiving NCMST does not experience the painful electrical sensations or shocks possible with ECT, thus avoiding the need for general anesthesia with its consequent morbid and mortal risks.
7. Because the invented method requires no patient electrical or mechanical contact, the patient receiving NCMST is not subjected to the risks of leakage currents, thereby eliminating the need for costly and time-consuming leakage current tests of the device.
8. Because no electrical stimuli or shocks are applied to the subject's head and the subject is not subject to a seizure, the method of NCEST is not "shock therapy", thus avoiding the prejudicial implications to some members of the public of this term.

DETAILED DESCRIPTION OF THE INVENTION

Figure 1:
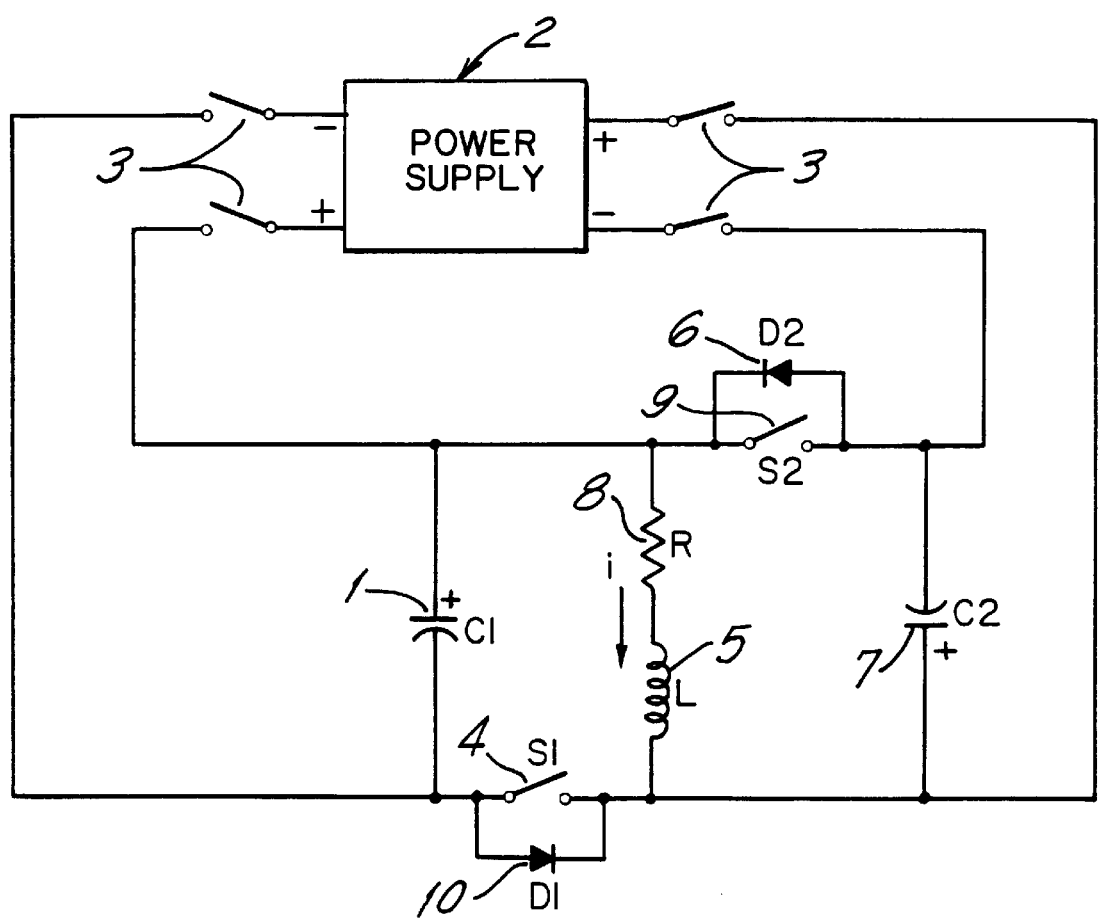
FIG. 1 a circuit diagram of a magnetic stimulator.

The magnetic stimulator circuit of FIG. 1 is suitable for a device to induce sufficient electrical currents in the living tissue of the brain of a human patient. Capacitor 1 (C1) is initially charged by a power supply 2 that is connected to capacitor 1 (C1) by solid state switches 3. When capacitor 1 (C1) reaches a sufficient charge, these switches 3 open and the power supply 1 is disconnected from the circuit. Switch 4 (S1) is then closed, completing a circuit loop containing capacitor 1 (C1) switch 4 (S1), inductor coil 5 (L) and resistor 8 (R). Resistor 8 (R) represents the combined resistance of the cables, switches, capacitors, and coil L, and ideally is very low. The closing of switch 4 (S1) allows the charge on capacitor 1 (C1) to be discharged through the coil 5 (L). The current, i, in the coil 5 reaches its maximum when the voltage on capacitor 1 (C1) reaches zero. At that moment, switch 4 (S1) is opened and the inductive force of coil 5 (L) turns on diode 6 (D2) and charges capacitor 7 (C2). Most of the initial charge on capacitor 1 (C1) will thus be transferred to capacitor 7 (C2) with relatively small losses due to the stimulation pulse. The power supply used to charge capacitor 1 (C1) is also switchable and is connected to capacitor 7 (C2) to "top off" capacitor 7 (C2). When capacitor 7 (C2) is fully charged, switch 9 (S2) closes and capacitor 7 (C2) discharges through the coil 5 (L) opening switch 9 (S2). When the voltage on capacitor 7 (C2) reaches zero inductor coil 5 (L) turns on diode 10 (D1) to "recharge" capacitor 1 (C1) and capacitor 7 (C2). The use of the inductive coil 5 (L) to recharge each capacitor 1 (C1) and 7 (C2) allows the capacitors to be recharged faster than using the power supply by itself. This allows for a higher pulse repetition rate. Having the coil 5 (L) discharge its inductive energy by charging the capacitor 1 (C1) and 7 (C2), whenever switches 4 (S1) and 9 (S2) are opened, avoids having the coil 5 (L) dissipate that inductive energy as heat. This allows the device to have low heat dissipation and requires little, if any, external cooling.

Figure 2:
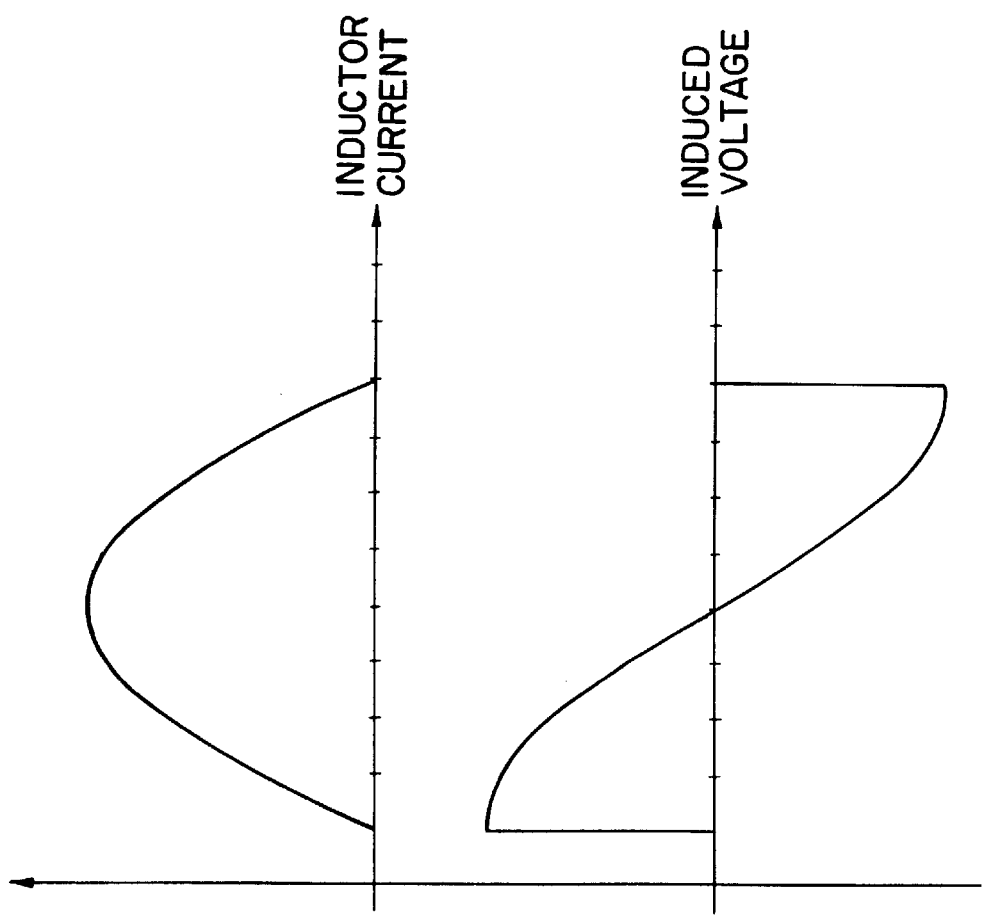
FIG. 2 illustrates the waveform of the current in the coil and the waveform of the voltage induced in the brain tissue.

The inductor current, shown in FIG. 2, is proportional to the magnetic field induced by the coil 5 (L). This magnetic field generates an induced voltage in the brain tissue (also shown in FIG. 2) that is proportional to the rate of change (i.e., the first derivative) of the magnetic field. This results in the single monophasic cosine induced voltage pulse of FIG. 2.

The method of the present invention applies the induced voltage pulses to selected focus points within the brain. By proper selection of pulse repetition rate, amplitude and duration, therapeutic results in the treatment of neuropsychiatric disorders may be achieved. In nonconvulsive magnetic stimulation (NCMST), the intended therapeutic agent is low energy excitation of surface and deep brain structures without inducing a generalized brain seizure. In magnetoconvulsive therapy (MCT), which is the subject of U.S. patent application Ser. No. 08/231,307 (allowed), incorporated by reference, high energy electrical fields are generated in the brain at selected foci to induce therapeutic brain seizures.

The strength of the magnetic field flux created by the coil 5 (L) will preferably be in the range of from 1 to 5 Teslas, and most preferably about 2 Teslas. For magnetic fluxes above 1 Tesla it may be necessary and more practical to use super-conducting magnets to minimize the size of the coil and power requirements. The superconductor magnet may be of the type used in magnetic resonance imaging (MRI) systems in which a liquid helium cryostat is used to refrigerate a Low-Te superconductive magnet.

Figure 3:
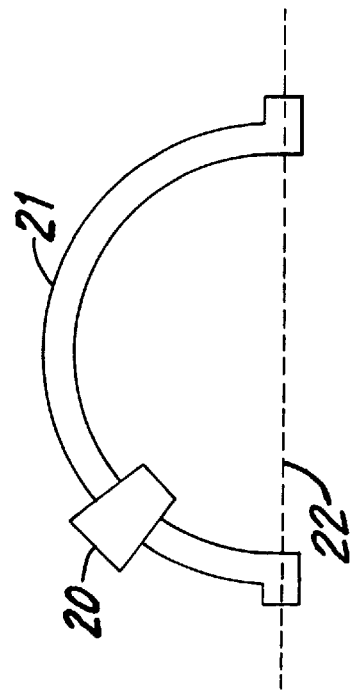
FIG. 3 is a top plan view of a magnetic stimulator system.

As shown in FIG. 3, the magnetic stimulation device may be housed in a Dewar container 20 that moves around the head on a semicircular track 21. The semicircular track 21 can then be pivotally mounted to allow the track to rotate about an imaginary axis 22 around the patient's head. This three dimensional positioning of the coil and the variance of the strength of the induced voltage allow the operator to induce electrical currents at a particular focal point within the brain.

Figure 4:
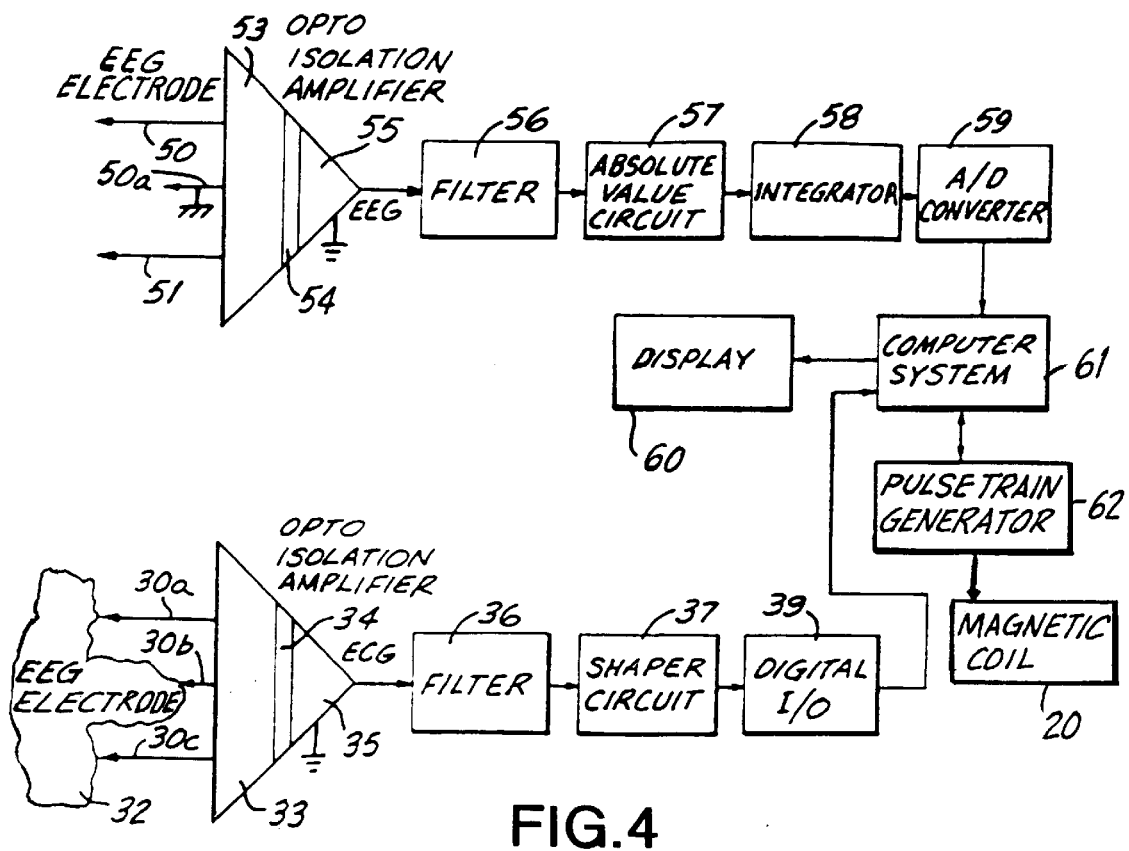
FIG. 4 is a block diagram of the device of the present invention-including ECG and EEG monitors.

In the embodiment shown in FIG. 4 the ECG signal (electrocardiograph), which detects heart activity, is sensed via three disposable or reusable electrodes 30a, 30b and 30c pasted on the chest 32 of the patient. The ECG signal is amplified with a low-noise differential amplifier 33 (less than one microvolt of noise) having a band width of 0–300 Hz. For patient safety the signal is isolated with optoelectronic isolator 34. The ECG signal is then further amplified by amplifier 35 and its frequency is then limited with a 2–50 Hz filter 36.

In one embodiment, to remove electromagnetic noise caused by the pulse train to the magnetic coil, a notch filter is used at the frequency of the pulse train. For example, if the pulse train is at 30 Hz a notch filter at 25–35 Hz is employed. Alternatively, or in addition, as explained below, ECG readings are taken only during pauses in the pulse train.

The signal is then passed through a shaper circuit 37 which detects the R-wave of the ECG and provides a square wave output compatible with detection by the digital circuitry of the computer system 38. The pulse output of shaper circuit 37 is connected to a digital input-output circuit 39 which provides a digital interrupt signal with every heartbeat, i.e., it is a rate detector. The heart rate is determined beat-to-beat by timing the interval between successive R-waves. The system will calculate heart rates and rates of change in heart rate and it will report these via the electronic alphanumeric display 60, or alternatively via a moving paper record. The system will calculate the time of the steepest drop in the heart rate. The pre-stimulus (baseline) frequency is determined over a 5-second period as a point of reference. After the operator delivers the treatment stimulus, by triggering a treatment switch on the device 41, the heart rate is followed. The time of occurrence of greatest deceleration is identified by comparing the beat-to-beat changes in heart rate. This time is then reported to the operator via the electronic alphanumeric display 60, or alternatively via a moving paper record. If the heart rate increases by a user selectable threshold value, such as at least 5% over prestimulus (baseline) frequency during or after the stimulus, or it accelerates positively or negatively by a user selectable threshold value such as 10 bpm per 5 sec, the operator is informed that there was observed effect on the heart rate.

In the embodiment shown in FIG. 4 the EEG signal is determined from two disposable or reuseable scalp electrodes 50 and 51 pasted over sites on the head 52, e.g., on the forehead, typically above the eyes, or over the mastoid processes, or above one eye and over one mastoid process. The EEG signal is then amplified with a differential instrumentation amplifier 53. To minimize unintended current exposure for patient safety, the signal is isolated with optoelectronic isolator 54. The EEG signal is then further amplified by amplifier 55 and its frequency is limited with a 2–25 Hz filter 56.

The pulsing of the coil 20 may cause electromagnetic radiation which is detected as noise by the EEG electrodes. It is helpful, to avoid such noise, that (i) the electrodes are shielded, and (ii) a notch filter is used at the frequency of the pulse train. For example, if the pulse train is at 30 Hz a notch filter at 25–35 Hz may be used.

Alternatively, or in addition, the EEG monitor is switched on only during pauses in the pulse train to the magnetic coil. For example, the pulse train is interrupted by 2–6 pauses. The computer system 61 controls the automatic switching (on and off) of the EEG monitor and controls the pulse train generated by the pulse train generator 62 to the magnetic coil 20. For example, the magnetic coil 20 is pulsed for 5 seconds, there is a pause of 1 second during which the EEG monitor is switched on and off for 0.9 second and this sequence is repeated 2–4 times.

The signal is then passed through an absolute value circuit 57 and an integrator 58 to provide the mean value of the EEG. The mean analog value is then sampled and digitized by an analog-to-signal (A/D) converter 59. The system will calculate the time of the steepest drop in the EEG voltage.

The patient's brain waves, as detected by the EEG electrodes 50, 50a, 51 and amplified and digitized by the EEG system, shown in FIG. 3, may be used to provide additional information to the operator. The EEG signal may be divided, by filters, into selected frequency bands within the 2–25 Hz band of filter 56. The Delta band is 2–3.5 Hz, the Theta band is 3.5–7.5 Hz, the Alpha band is 7.5–12.5 Hz and the lower portion of the Beta band is 12.5–25 Hz. Preferably the "absolute power" in the Delta band (2–3.5 Hz) is measured, although alternatively or in addition absolute power across the entire 2–25 Hz spectrum may be measured or absolute power in the other bands may be measured. The "absolute power" is the mean integrated voltage in the selected band taken over the duration of the treatment. The absolute power in the Delta band is called the "Delta Energy Index". The "energy" is power times the number of seconds. That index is displayed to the operator at the end of the treatment and printed in an end-of-treatment report. Alternatively, a "Total Energy Index" may be obtained, displayed and printed-out, based upon the absolute power measured by the mean integrated voltage across the entire band 2–25 Hz and taken over the duration of the treatment.

The pulse train to the coil is halted, either automatically under computer control, or manually by the operator, if the ECG or EEG monitors indicate an incipient EEG seizure. Preferably an age-related norm (normal population group) is obtained for the power in each EEG band and total power. These norms are used to set predetermined threshold values. If there is (i) an increase in coherence, and/or (ii) an increase in EEG voltage, in any band, or total EEG power; and/or (iii) an increase in individual EEG spikes, which is beyond the predetermined threshold values, there may be an indication of incipient seizure. For example, if the EEG power in the Delta band of the patient is 20% above the mean normal power, in view of the patient's age, and there are EEG spikes, there may be an incipient seizure and the pulse train is halted. Preferably a computer software program recognizes the indications of incipient seizure by comparison of the patient's EEG with the predetermined threshold values and generates a control signal to halt the pulse train when one, or more, of the EEG signals exceed the predetermined threshold values.

Figure 5:
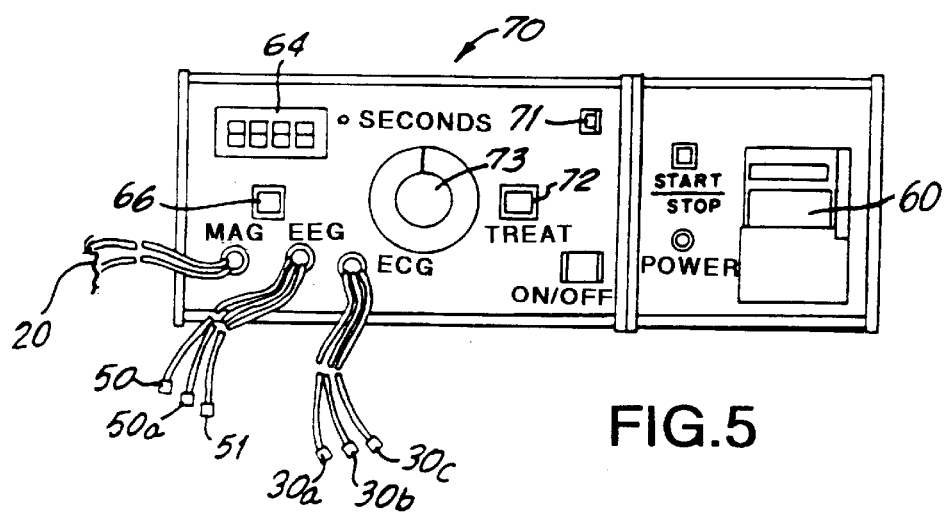
FIG. 5 is a front view of the device of the present invention.

As shown in FIG. 5, the magnetic stimulation device 70 includes a magnetic stimulator, EEG monitor, ECG monitor, computer system 61 and display 60. The ECG monitor has three electrode leads 30a–30c; the EEG monitor has three electrode leads 50, 51, 50a, and the magnetic stimulator has two leads to the coil 20. The computer system 61 controls the magnetic stimulation and performs the EEG and ECG analysis and presents results on the display 60. The dial 73 is used to control time (seconds of magnetic stimulation) and the seconds are shown on number display 64. The alarm 66 is lighted, and a buzzer sounds, if the patient shows signals of an adverse effect. The light 72 is lit during treatment periods.

What is claimed is:

1. A method in medicine to induce a non-convulsive magnetic stimulation (NCMST) without a convulsive brain seizure in a human patient in order to treat the patient's psychiatric disorder using a combined magnetic stimulator, ECG (electrocardiograph) monitor and EEG (electroencephalograph) monitor, the method comprising:

positioning a magnetic induction coil proximate the head of the patient;

flowing a pulse train of electrical waveforms through the coil to produce a sufficient and varying magnetic field to generate a sufficient electrical stimulus in the patient's brain to induce a therapeutic effect without inducing a convulsive brain seizure;

monitoring the heart beat of the patient using the ECG monitor;

monitoring the brain waves of the patient using the EEG monitor; and halting the varying magnetic field if the ECG or EEG monitors indicate the onset of a convulsion or other adverse effect.

2. A method as in claim 1 and prior to flowing the pulse train, pretreating the patient with an anticonvulsant pharmaceutical agent to inhibit the development or spread of partial or generalized seizure activity.

3. A method as in claim 1 and halting the varying magnetic field on an increase in EEG coherence above a predetermined amount.

4. A method as in claim 1 and halting the varying magnetic field on an increase in the EEG voltage and the occurrence of individual EEG spikes.

5. A method in medicine as in claim 1 wherein the pulse train consists of a series of waves and is greater than 2000 amps in electrical current and less than 5000 amps, the pulse train is in the range of 10–20 seconds in duration, each wave is less than 1 millisecond in duration, and the magnetic field produced thereby is at least 1 Tesla.

6. A method as in claim 1 wherein the magnetic induction coil is a superconductive coil cooled below its critical temperature.

7. A method as in claim 1 wherein the pulse train is in the range of 10–20 seconds in duration and is at a frequency in the range of 25–50 Hz.

8. A method as in claim 1 wherein the pulses have a pulse duration in the range of 100 to 300 microseconds, whether constant or varying systematically or nonsystematically within said range.

9. A device to induce a non-convulsive magnetic stimulation (NCMST) without a convulsive brain seizure in a human patient in order to treat the patient's psychiatric disorder being a combined magnetic stimulator, ECG (electrocardiograph) monitor and EEG (electroencephalograph) monitor, the device comprising:

a magnetic stimulator including a magnetic induction coil adapted to be positioned proximate the head of the patient, and pulse train means to flow a pulse train of electrical waveforms through the coil to produce a sufficient and varying magnetic field to generate a sufficient electrical stimulus in the patient's brain to induce a therapeutic effect without inducing a convulsive brain seizure;

an ECG monitor to monitor heart beats of the patient during the magnetic stimulation; and an EEG monitor to monitor the brain waves of the patient during the magnetic stimulation.

10. A device as in claim 9 and means for halting the varying magnetic field if the ECG or EEG monitors indicate the onset of a convulsion or other adverse effect.

11. A device as in claim 9 wherein the pulse train consists of a series of waves and is greater than 2000 amps in electrical current and less than 5000 amps, the pulse train is in the range of 10–20 seconds in duration, each wave is less than 1 millisecond in duration, and the magnetic field produced thereby is at least 1 Tesla.

12. A device as in claim 9 wherein the magnetic induction coil is a superconductive coil cooled below its critical temperature.

13. A device as in claim 9 wherein the pulse train is in the range of 10–20 seconds in duration and is at a frequency in the range of 25–50 Hz.

14. A device as in claim 9 wherein the pulses have a pulse duration in the range of 100 to 300 microseconds, whether constant or varying systematically or nonsystematically within said range.

* * * * *